US012259379B2

(12) United States Patent
Iwahori et al.

(10) Patent No.: US 12,259,379 B2
(45) Date of Patent: Mar. 25, 2025

(54) METHOD FOR PREDICTING EFFECT OF TUMOR IMMUNOTHERAPY USING TUMOR CYTOTOXIC ACTIVITY OF PERIPHERAL BLOOD T CELLS AS INDEX (71) Applicant: OSAKA UNIVERSITY, Suita (JP)

(72) Inventors: Kota Iwahori, Suita (JP); Hisashi Wada, Suita (JP)

(73) Assignee: OSAKA UNIVERSITY, Suita (JP)

( * ) Notice: Subject to any disclaimer, the term of this patent is extended or adjusted under 35 U.S.C. 154(b) by 432 days.

(21) Appl. No.: 16/626,683

(22) PCT Filed: Jun. 29, 2018

(86) PCT No.: PCT/JP2018/024770
§ 371 (c)(1),
(2) Date: Dec. 26, 2019

(87) PCT Pub. No.: WO2019/004415
PCT Pub. Date: Jan. 3, 2019

(65) Prior Publication Data
US 2020/0116700 A1    Apr. 16, 2020

(30) Foreign Application Priority Data

Jun. 30, 2017  (JP) ................. 2017-128621
Dec. 25, 2017  (JP) ................. 2017-247780

(51) Int. Cl.
G01N 33/50      (2006.01)
A61K 39/395     (2006.01)
C07K 16/28      (2006.01)
C07K 16/30      (2006.01)
G01N 33/53      (2006.01)
G01N 33/574     (2006.01)
G16B 50/30      (2019.01)
G16H 50/30      (2018.01)
A61K 39/00      (2006.01)

(52) U.S. Cl.
CPC .......... G01N 33/5011 (2013.01); C07K 16/30 (2013.01); G16B 50/30 (2019.02); G16H 50/30 (2018.01); A61K 2039/505 (2013.01); C07K 2317/31 (2013.01); G01N 2800/52 (2013.01)

(58) Field of Classification Search
CPC ............. G01N 33/5011; G01N 33/574; G01N 2800/52; C07K 16/30; C07K 2317/31; A61K 2039/505
See application file for complete search history.

(56) References Cited

U.S. PATENT DOCUMENTS

2008/0152631 A1   6/2008  Sugiyama
2019/0170752 A1*  6/2019  Luo .................. A61P 35/00

FOREIGN PATENT DOCUMENTS

| CN | 103865998 A    | 6/2014  |
| EP | 1306431 A1     | 5/2003  |
| JP | 2009-521474 A  | 6/2009  |
| JP | 2016-531907 A  | 10/2016 |
| WO | 2005/095598 A1 | 10/2005 |
| WO | 2007/073499 A2 | 6/2007  |
| WO | 2014/138306 A1 | 9/2014  |
| WO | 2015/016718 A1 | 2/2015  |

OTHER PUBLICATIONS

Wu et al., Blinatumomab: a bispecific T cell engager (BiTE) antibody against CD19/CD3 for refractory acute lymphoid leukemia, Journal of Hematology & Oncology, 2015, 8:104 (7 pages).*
Lejeune et al. Frontiers in Immunology, 2020, 99, article 762, pp. 1-20.*
Nociari et al., J Immunol Methods, 1998, 213:157-167.*
Almagro et. al., Frontiers in Immunology, 2018, 8: 1751, pp. 1-19.*
Herold et al. (Science Reports, 2017, 7(1):12276, pp. 1-17.*
Murphy et al., Journal of Immunological Methods, 2018, 463: 127-133.*
Extended European search report dated May 25, 2020 for European Patent Application No. 18824344.8, 9 Pages.
Torisu-Itakura et al., "Redirected Lysis of Human Melanoma Cells by a MCSP/CD3-bispecific BiTE Antibody That Engages Patient-derived T Cells", Journal of Immunotherapy, Oct. 2011, vol. 34, No. 8, pp. 597-605.
Nazarian et al., "Characterization of Bispecific T-cell Engager (BiTE) Antibodies with a High-Capacity T-cell Dependent Cellular Cytotoxicity (TDCC) Assay", Journal of Biomolecular Screening, 2015, vol. 20, No. 4, pp. 519-527.
Hipp et al., "A novel BCMA/CD3 bispecific T-cell engager for the treatment of multiple myeloma induces lysis in vitro and in vivo", Leukemia, 2017, vol. 31, No. 8, pp. 1743-1751.
Zou et al., "Immunotherapy based on bispecific T-cell engager with hIgG1 Fc sequence as a new therapeutic strategy in multiple myeloma", Cancer Science, 2015, vol. 106, No. 5, pp. 512-521.
Office Action dated Sep. 21, 2022 for corresponding Chinese Application No. 201880043689.2, 15 pages including English translation.
Masucci et al., "Validation of biomarkers to predict response to immunotherapy in cancer: vol. I—pre-analytical and analytical validation," Journal for Immuno Therapy of Cancer, (2016) vol. 4, No. 76, pp. 1-25.

(Continued)

Primary Examiner — Hong Sang
(74) Attorney, Agent, or Firm — MH2 Technology Law Group, LLP (57) ABSTRACT An object of the present invention is to provide a companion diagnostic for predicting the effect of a tumor immunotherapy. The effect of a tumor immunotherapy is predicted by a method including step 1: contacting directly or indirectly peripheral blood mononuclear cells collected from a patient who is a target for treatment of a malignant tumor with tumor cells in vitro; step 2: determining whether the tumor cells that contacted with the peripheral blood mononuclear cells in step 1 are damaged; and step 3: determining that the tumor immunotherapy is effective against the malignant tumor in the patient when the tumor cells are determined to have been damaged in step 2.

8 Claims, 9 Drawing Sheets (56) References Cited

OTHER PUBLICATIONS

Akiyama et al., "Immunological effects of the anti-programmed death-1 antibody on human peripheral blood mononuclear cells," International Journal of Oncology, vol. 4949 (2016), pp. 1099-1107.

Plieth et al., "PD-1/PD-L1 Combination Therapies," Evaluate, Nov. 2015, pp. 1-16.

Schreiner et al., "Expression of inhibitory receptors on intratumoral T cells modulates the activity of a T cell-bispecific antibody targeting folate receptor," OncoImmunology, (2016) vol. 5, No. 2, 11 pages.

Goere et al., "Potent Immunomodulatory Effects of the Trifunctional Antibody Catamaxomab," Cancer Research (Jun. 4, 2016) vol. 73, No. 15, pp. 4664-4673.

Dako, "SK006, 50 tests for use with Autostainer Link 48", PD-L1 1 HC 22C3 pharmDx, Sep. 10, 2017, 21 pages.

Dijkstra et al., "Generation of Tumor-Reactive T Cells by Co-culture of Peripheral Blood Lymphocytes and Tumor Organoids," Cell (Sep. 6, 2018) vol. 174, No. 6, pp. 1586-1598.

Kenji Chamoto, "PD-1/PD-L1 Predictive biomarkers for anti-PD-1. PD-L1 antibody therapy," Journal of Molecular X Targeted Therapy for Cancer (2016) vol. 13, No. 4, pp. 485-489, with English Abstract.

International Search Report dated Oct. 2, 2018 from International Application No. PCT/JP2018/024770, 4 pages, including English translation.

\* cited by examiner

Fig.1

Collect PBMCs from peripheral blood of a patient who is a target for treatment of malignant tumor Co-culture with tumor cells ● T cells contained in PBMCs ▨ Tumor cells X Engager Measurement of tumor-cytotoxic activity

METHOD FOR PREDICTING EFFECT OF TUMOR IMMUNOTHERAPY USING TUMOR CYTOTOXIC ACTIVITY OF PERIPHERAL BLOOD T CELLS AS INDEX

CROSS-REFERENCE TO RELATED APPLICATIONS

This application is a U.S. National Stage application of PCT/JP2018/024770 filed 29 Jun. 2018, which claims priority to Japanese Application No. 2017-128621 filed 30 Jun. 2017 and Japanese Application No. 2017-247780 filed 25 Dec. 2017, the entire disclosures of which are incorporated herein by reference.

TECHNICAL FIELD

The present invention relates to a prediction method, a prediction device, and a computer program for prediction of the effect of a tumor immunotherapy using the tumor-cytotoxic activity of peripheral blood T cells as an index.

BACKGROUND ART

A tumor immunotherapy is a tumor treatment therapy that makes use of patients' immune response to tumor cells. In an example of tumor immunotherapy, a tumor patient's own cytotoxic T cells are activated using anti-CTLA-4 antibody, anti-PD-1 antibody, etc., which bind to proteins on the T cells, to kill the cancer cells by this function (NPL 1 and NPL 2).

Additionally, a method of specifically engaging cytotoxic T cells with tumor cells has been developed so that cytotoxic T cells present in a tumor tissue can efficiently exhibit cytotoxic activity against tumor cells. An engager currently used is a bispecific molecule that specifically recognizes, on a single molecule basis, the cell surface marker of a tumor cell and the surface marker of a T cell (NPL 2 and NPL 3).

CITATION LIST

Non-Patent Literature

NPL 1: PD1/PD-L1 Combination Therapies, 2015, Evaluate Ltd.
NPL 2: ONCOIMMUNOLOGY, 2016, VOL. 5, NO. 2, e1062969
NPL 3: Cancer Research, 2013, 73(15) August 1, pp. 4663-4673

SUMMARY OF INVENTION

Technical Problem

However, the response rate of, for example, pembrolizumab (trade name: Keytruda), which is a therapeutic agent used in tumor immunotherapy for non-small-cell lung cancer covered by insurance, is 19%; in fact, pembrolizumab is ineffective for many patients. For this reason, companion diagnostics have been performed to select a patient group for which the therapeutic agent of the tumor immunotherapy is effective. Although PD-L1 staining that uses a biopsy specimen is currently used as a companion diagnostic agent for pembrolizumab, the response rate is 45% even in the patient group positive in PD-L1 staining (50% or greater). Thus, there is strong demand for the development of companion diagnostics superior to PD-L1 staining.

Such response rates and difficulty in predicting the effect of a tumor immunotherapy are common problems in many cancer immunotherapies. Given the current state of tumor immunotherapies, an object of the present invention is to provide a companion diagnostic for predicting the effect of a tumor immunotherapy.

Solution to Problem

The present inventors conducted extensive research and found that the effect of a tumor immunotherapy can be predicted in a simple manner by measuring tumor-cytotoxic activity using mononuclear cells in peripheral blood in vitro.

The present invention was completed on the basis of this finding, and includes the following subject matter.

Item 1

A method for predicting an effect of a tumor immunotherapy, the method comprising
step 1: contacting directly or indirectly peripheral blood mononuclear cells collected from a patient who is a target for treatment of a malignant tumor with tumor cells in vitro,
step 2: determining whether the tumor cells that contacted with the peripheral blood mononuclear cells in step 1 are damaged, and
step 3: determining that the tumor immunotherapy is effective against the malignant tumor in the patient when the tumor cells are determined to have been damaged in step 2.

Item 2

The method according to Item 1, wherein in step 1, the peripheral blood mononuclear cells collected from the patient who is a target for treatment of a malignant tumor contact with the tumor cells indirectly via an engager in vitro.

Item 3

The method according to Item 1 or 2, wherein the step of determining whether the tumor cells are damaged comprises
the step of obtaining a value that reflects the tumor-cytotoxic activity by measuring tumor-cytotoxic activity of the peripheral blood mononuclear cells that contacted with the tumor cells, and
the step of comparing the value that reflects the tumor-cytotoxic activity with a corresponding reference value and determining that the tumor cells are damaged when the value is higher than the corresponding reference value.

Item 4

The method according to Item 2 or 3, wherein the engager is a bispecific molecule.

Item 5

The method according to Item 4, wherein the bispecific molecule contains an antigen-binding domain that binds to at least one member of T cell surface antigens and an antigen-binding domain that binds to at least one member of surface antigens of the tumor cells.

Item 6

The method according to any one of Items 1 to 5, wherein the tumor cells are a cultured cell line derived from a malignant tumor.

Item 7

A test reagent for predicting an effect of a tumor immunotherapy, which is for use in performing the method of any one of Items 2 to 6,
the test reagent comprising an engager.

Item 8

A test kit for predicting an effect of a tumor immunotherapy, the test kit comprising the test reagent of Item 7.

Item 9
A computer program for predicting an effect of a tumor immunotherapy, the computer program causing a computer to execute the steps of:
obtaining a measurement value of tumor-cytotoxic activity from tumor cells that directly or indirectly contacted with peripheral blood mononuclear cells collected from a patient who is a target for treatment of a malignant tumor in vitro,
determining whether the tumor cells are damaged on the basis of the measurement value, and
determining that the tumor immunotherapy is effective against the malignant tumor in the patient when the tumor cells are determined to have been damaged in the previous step.

Item 10
A storage medium in which the computer program of Item 9 is stored.

Item 11
A prediction device for predicting an effect of a tumor immunotherapy, the prediction device comprising at least a processing unit, wherein the processing unit
obtains a measurement value of tumor-cytotoxic activity from tumor cells that directly or indirectly brought contacted with peripheral blood mononuclear cells collected from a patient who is a target for treatment of a malignant tumor in vitro,
determines whether the tumor cells are damaged on the basis of the measurement value, and
determines that the tumor immunotherapy is effective against the malignant tumor in the patient when the tumor cells are determined to have been damaged.

Advantageous Effects of Invention

The present invention has enabled the prediction of the effect of a tumor immunotherapy in a simple manner by measuring tumor-cytotoxic activity in vitro using peripheral blood mononuclear cells (PBMC).

DESCRIPTION OF EMBODIMENTS

1. A Method for Predicting the Effect of a Tumor Immunotherapy

Figure 1:
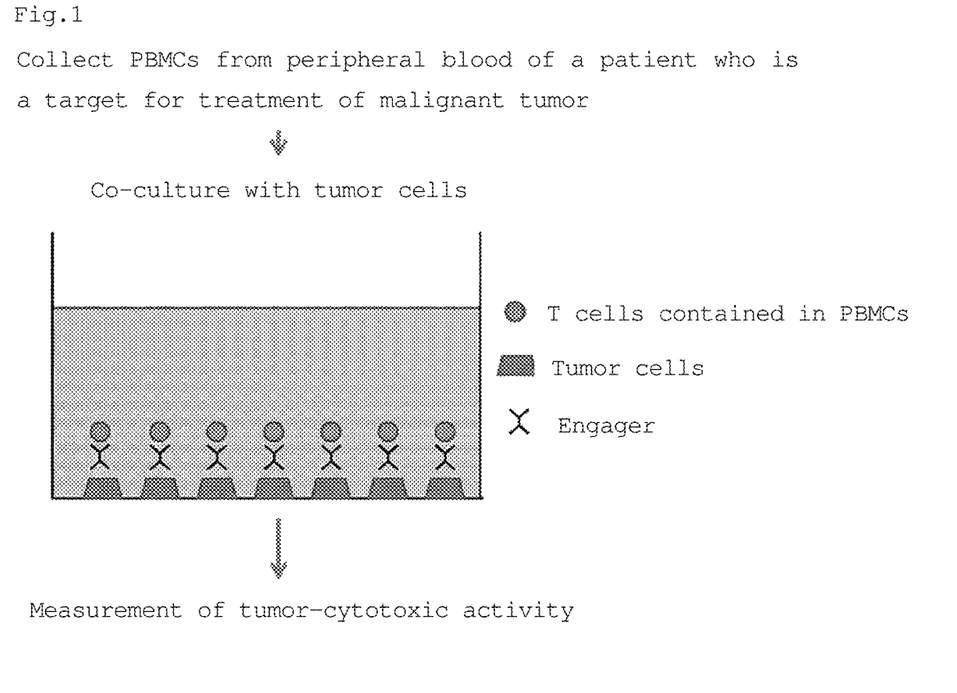
FIG. 1 illustrates an outline of the present invention.
Figure 2:
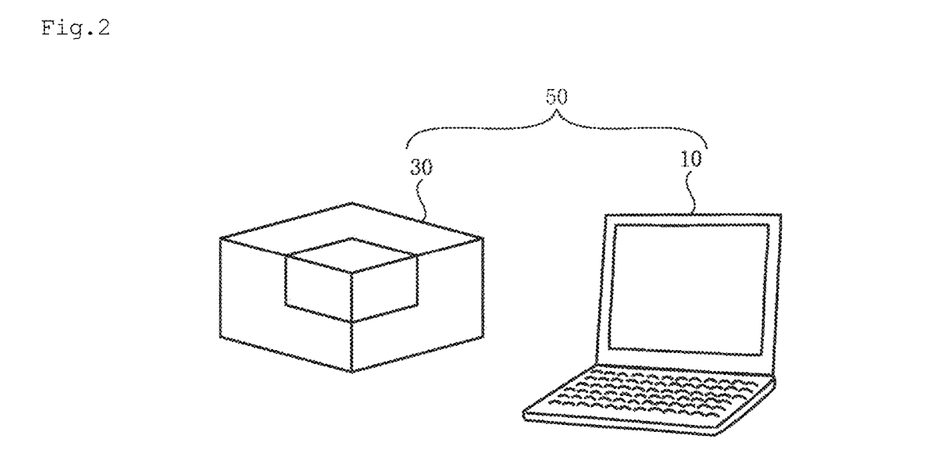
FIG. 2 illustrates an outline of a prediction device.

The first embodiment of the present invention relates to a method for predicting the effect of a tumor immunotherapy. First, an outline of this embodiment is described with reference to FIG. 1. As illustrated in FIG. 1, in this embodiment, peripheral blood mononuclear cells (PBMC) collected from a patient who is a target for treatment of a malignant tumor contact with tumor cells directly or indirectly via an engager in vitro and cultured; how much the tumor cells have been damaged by the PBMCs (tumor-cytotoxic activity) is then measured to predict the effect of a tumor immunotherapy on the tumor patient on the basis of the measurement value. FIG. 1 illustrates an example in which T cells contained in PBMCs contact with tumor cells that have been seeded and cultured in a Petri dish beforehand via an engager.

More specifically, this embodiment relates to a method for predicting the effect of a tumor immunotherapy comprising the step of directly or indirectly contacting PBMCs collected from a patient who is a target for treatment of a malignant tumor with tumor cells in vitro (step 1), the step of determining whether tumor cells that contacted with PBMCs in step 1 are damaged (step 2), and the step of determining that the tumor immunotherapy is effective against the malignant tumor in the patient when the tumor cells are determined to have been damaged in step 2 (step 3).

In the present invention, the tumor immunotherapy can be any tumor immunotherapy that is a method for treating a tumor by increasing the tumor-cytotoxic activity of T cells. The tumor immunotherapy according to the present invention includes immune checkpoint inhibitor therapies, such as anti-PD1 antibody, anti-PD-L1 antibody, anti-CCR4 antibody, anti-CTLA-4 antibody, anti-Tim3 antibody, and anti-LAG3 antibody; adoptive immunotherapies, in which, for example, chimeric antigen receptor-T cells are administered; cytokine therapies, such as one using interleukin 2; tumor vaccine therapies, in which, for example, a protein or peptide derived from a tumor antigen (e.g., WT-1, NY-ESO-1) is administered; and bispecific T cell engager (or BiTE®) or bispecific antibody therapies.

In the present invention, the tumor includes a malignant tumor and a benign tumor, and is preferably a malignant tumor. The tumor also includes an epithelial tumor and a non-epithelial tumor, and is preferably an epithelial tumor. In the present invention, the tumor is most preferably an epithelial malignant tumor.

Examples of malignant tumors include respiratory-system malignant tumors, which develop in the trachea, bronchus, lung, etc.; gastrointestinal malignant tumors, which develop in the upper pharynx, esophagus, stomach, duodenum, jejunum, ileum, cecum, appendix, ascending colon, transverse colon, sigmoid colon, rectum, anal region, etc.; liver cancer; pancreatic cancer; urological malignant tumors, which develop in the bladder, ureter, or kidney; female-reproductive-system malignant tumors, which develop in the ovary, fallopian tube, uterus, etc.; breast cancer; prostate cancer; skin cancer; endocrine-system malignant tumors, such as the hypothalamus, pituitary gland, thyroid gland, parathyroid gland, and adrenal gland; central-nervous-system malignant tumors; solid tumors, such as malignant tumors that develop in the bone and soft tissue, hematopoietic malignant tumors, such as of myelodysplastic syndrome, acute lymphocytic leukemia, acute myeloid leukemia, chronic lymphocytic leukemia, chronic myeloid leukemia, acute myelomonocytic leukemia, chronic myelomonocytic leukemia, acute monocytic leukemia, chronic monocytic leukemia, acute promyelocytic leukemia, acute megakaryocytic leukemia, erythroleukemia, eosinophilic leukemia, chronic eosinophilic leukemia, chronic neutrophilic leukemia, adult T-cell leukemia, hairy cell leukemia, plasma cell leukemia, multiple myeloma, and malignant lymphoma; and hematopoietic organ tumors, such as lymphatic-system malignant tumors. More preferable examples of malignant tumors include respiratory-system epithelial malignant tumors, such as lung cancer (squamous-cell cancer, small-cell cancer, large-cell cancer, adenocarcinoma); gastrointestinal epithelial malignant tumors, such as stomach cancer, duodenal cancer, colorectal cancer (e.g., sigmoid colon cancer, and rectal cancer); liver cancer; pancreatic cancer; bladder cancer; thyroid cancer; ovarian cancer; breast cancer; and prostate cancer. Most preferably, a malignant tumor is lung cancer.

In the present invention, the "patient who is a target for treatment of a malignant tumor" can be any patient as long as a tumor immunotherapy is applicable to the patient. Examples of such a patient include a patient with a tumor among those listed above who has yet to be treated, a patient who has already been treated for a tumor, a patient currently in treatment of a tumor, and a patient who has experienced a recurrence or developed metastasis. The treatment of a tumor preferably includes surgical tumor resection, chemotherapy (more preferably, chemotherapy with administration of an antitumor agent other than a tumor immunotherapy), and radiation therapy.

In the present invention, the peripheral blood can be any peripheral blood as long as mononuclear cells containing T cells can be obtained from the peripheral blood. The peripheral blood may be arterial blood or venous blood, and is preferably venous blood. Peripheral blood can be collected, for example, from the blood vessel of a limb. Peripheral blood may be collected from the blood vessel of a body part other than a limb during surgery or a biopsy.

The method for collecting peripheral blood can be any method by which mononuclear cells can be obtained; it is preferable to collect peripheral blood using an anticoagulant. The anticoagulant includes ethylenediaminetetraacetate, citrate, and a heparin salt, with heparin salt being preferable.

PBMCs can be collected in accordance with a known method. For example, PBMCs can be collected by centrifugation using a specific-gravity solution (with a density of about 1.077±0.001 g/ml) for separating human lymphocytes. Red blood cells in peripheral blood may be hemolyzed using a hemolyzing agent, and the obtained nucleated cells may be used as PBMCs. Desired cells may be collected using a cell sorter or by magnetic-activated cell sorting. Examples of desired cells include T cells, with $CD3^+$ T cells or $CD8^+$ T cells being preferable.

The tumor cells that contact with PBMCs can be any tumor cells derived from a tumor among those listed above. The tumor cells are preferably cultured cell lines. The cultured cell lines can be any cultured cell lines, and include, for example, a cultured cell line derived from a malignant tumor, such as U251 cell line, RERF cell line, or A549 cell line. The tumor cell is not necessarily of the same type as that of the malignant tumor in the patient, but may be of the same type. The tumor cell is preferably a cell that can grow under the same culture conditions as those for PBMCs.

The method for contacting PBMCs with tumor cells in vitro can be any method as long as PBMCs directly or indirectly contact with tumor cells.

When PBMCs and tumor cells contact with each other in vitro, the tumor cells are preferably seeded in a plate or culture bottle beforehand in vitro. When the tumor cells are adhesive cells, the tumor cells are more preferably adhered to a Petri dish or culture bottle in a viable condition in vitro. Additionally, when the tumor cells are adhesive cells, the tumor cells are preferably those that have been cultured for about 12 hours to 48 hours under growth conditions (e.g., at 35° C. to 37° C. in about 5% $CO_2$ gas). A culture medium for culturing the tumor cells can be any culture medium that allows the tumor cells to remain viable or grow. Examples of the culture medium include a RPMI1640 medium (including a modified medium thereof), an α-MEM medium (including a modified medium thereof), and a Dulbecco's MEM medium (including a modified medium thereof), all of which contain about 8% to 20% of fetal bovine serum.

Regarding the cell count in contacting PBMCs and tumor cells with each other, for example, about $1 \times 10^3$ to $1 \times 10^5$, preferably about $5 \times 10^3$ to $5 \times 10^4$, of tumor cells preferably contact with about $1 \times 10^3$ to $1 \times 10^5$, preferably about $5 \times 10^3$ to $5 \times 10^4$, of PBMCs, per well of a 96-well plate.

The method for directly contacting PBMCs and tumor cells with each other includes a method of seeding PBMCs in a plate or culture bottle in which tumor cells have been seeded. Preferably, when seeded PBMCs are floating, centrifugation may be performed at about 1,000 to 2,000 rpm for about 5 to 10 minutes.

The method for indirectly contacting PBMCs and tumor cells with each other includes a method of contacting PBMCs and tumor cells with each other via an engager. In this embodiment, the engager can be any engager that is a molecule capable of engaging PBMCs, preferably lymphocytes, more preferably T cells, still more preferably CD8+ T cells (cytotoxic T cells) with tumor cells. "Engage" refers to crosslinking at least a cell with a cell (e.g., a T cell with a tumor cell), and preferably refers to the state in which a cytotoxic T cell exhibits cytotoxic activity on a tumor cell with which the cytotoxic T cell is crosslinked.

Preferable engagers include a bispecific molecule and a trispecific molecule. More preferable engagers include a bispecific molecule. The bispecific molecule and the trispecific molecule are each preferably a molecule that contains an antigen-binding domain that binds to at least one member of surface antigens of a T cell and an antigen-binding domain that binds to at least one member of surface antigens of a tumor cell. The antigen-binding domain can be any antigen-binding domain that binds to a target antigen. The antigen-binding domain contains, for example, at least one CDR selected from the group consisting of complementarity-determining region 1 (CDR1), complementarity-determining region 2 (CDR2), and complementarity-determining region 3 (CDR3) of an immunoglobulin that binds to the antigen. The antigen-binding domain preferably contains at least two CDRs selected from the group consisting of CDR1, CDR2, and CDR3, and more preferably contains CDR1, CDR2, and CDR3. The CDRs may be derived from a heavy chain of an immunoglobulin or from a light chain of an immunoglobulin. More preferably, each CDR in the antigen-binding domain may be adjacent to its corresponding framework region. The antigen-binding domain may be a variable region (V region) of an immunoglobulin, sc-Fv, a Fab fragment of an immunoglobulin, or the like.

The number of antigen-binding domains that bind to at least one member of surface antigens may be one, two, or more per antigen. For example, the antigen-binding domain that binds to at least one member of surface antigens may be a combination of Fab fragments of the same type, a combination of variable regions of the same type, a combination of sc-Fv of the same type, a combination of a heavy chain Fab fragment and a light chain Fab fragment derived from one antibody, a combination of a heavy-chain variable region and a light-chain variable region derived from one antibody, or a combination of a heavy chain and sc-Fv derived from one antibody.

The surface antigens of a T cell are present on the surface of the T cell; the surface antigens can be any surface antigen as long as at least one antigen-binding domain present in a bispecific molecule or a trispecific molecule can bind to one of the surface antigens. The surface antigens of a T cell preferably include the surface antigens of a cytotoxic T cell. Examples of surface antigens of a T cell include CD3, CD8, TCR, CTLA-4, PD1, Tim3, CD27, CD28, CD40, CD134 (OX40), CD137 (4-1BB), and CD278 (ICOS), with CD3 being preferable.

The surface antigens of a tumor cell are present on the surface of the tumor cell; the surface antigens can be any surface antigen as long as at least one antigen-binding domain present in a bispecific molecule or a trispecific molecule can bind to one of the surface antigens. The surface antigens of a tumor cell include EphA1 (ephrin type-A receptor 1), EphA2, FolR1 (folate receptor 1), EpCAM (epithelial cell adhesion molecule), CD19, Her1 (v-erb-b2 erythroblastic leukemia viral oncogene homolog 1: ErbB1), Her2, CD20, EGFR (epidermal growth factor receptor), CCR4 (C-C chemokine receptor type 4), CEA (carcinoembryonic antigen), GD2, GD3, CD22, CD30, CD33, CD70, CD123, EGFRvIII, MUC1 (Mucinl), PSCA (prostate stem cell antigen), PSMA (prostate-specific membrane antigen), HLA-A1+NY-ESO1 (HLA-A1 restricted NY-ESO1), HLA-A2+NY-ESO1 (HLA-A2 restricted NY-ESO1), and HLA-A3+NY-ESO1 (HLA-A3 restricted NY-ESO1).

The bispecific molecule includes a bispecific T-cell engager and a bispecific antibody. The bispecific T-cell engager includes an engager that targets CD19 and CD3, and an engager that targets EphA2 and CD3. The bispecific antibody also include an antibody that targets EpCAM and CD3.

Regarding the cell count in contacting PBMCs and tumor cells with each other, for example, about $1\times10^3$ to $1\times10^5$, preferably about $5\times10^3$ to $5\times10^4$, of tumor cells preferably contact with about $1\times10^3$ to $1\times10^5$, preferably about $5\times10^3$ to $5\times10^4$, of PBMCs, per well of a 96-well plate. When a bispecific molecule is added, it is preferable to add the bispecific molecule to give a final concentration of 50 to 200 ng/ml per well of a 96-well plate.

The direct or indirect contact between PBMCs and tumor cells is preferably performed under such conditions that PBMCs and tumor cells are individually able to grow in a normal manner. For example, the contact can be performed under growth conditions (e.g., at 35° C. to 37° C. in about 5% $CO_2$ gas) for about 16 hours to 72 hours, preferably about 36 to 50 hours. The culture medium for use in contacting PBMCs with tumor cells can be any culture medium as long as PBMCs and tumor cells can remain viable, or can grow in the medium. Examples of such a medium include a RPMI1640 medium (including a modified medium thereof) containing about 8% to 20% of fetal bovine serum.

Subsequently, cytotoxic activity is measured. The method for measuring cytotoxic activity can be any method as long as the method can evaluate the degree to which PBMCs have damaged tumor cells. For example, when PBMCs and tumor cells directly contact with each other, cytotoxic activity can be determined from the viable cell count immediately after PBMCs and tumor cells contacted and the viable cell count after 48 hours since PBMCs and tumor cells contacted. When PBMCs and tumor cells indirectly contact via an engager, wells to which an engager is added when contacting PBMCs and tumor cells with each other (measured wells) and wells to which an engager is not added when contacting PBMCs and tumor cells with each other (negative control wells) are prepared; the viable cell count of the measured wells and the viable cell count of the negative control wells are compared, and a value that reflects tumor-cytotoxic activity is obtained. For example, a value that reflects tumor-cytotoxic activity can be determined from the following equation.

$$\text{Tumor-cytotoxic activity } (\%) = \{([\text{viable cell count of negative control wells}] - [\text{viable cell count of measured wells}]) / [\text{viable cell count of negative control wells}]\} \times 100$$

For example, when the viable cell count is determined using a living-cell-staining reagent, such as CellTiter 96® AQueous One Solution Reagent (MTS reagent: Promega Corporation), the absorbance of each well, instead of the viable cell count, may be used as a value that reflects tumor-cytotoxic activity.

Whether tumor cells are damaged can be determined by comparing the value that reflects tumor-cytotoxic activity with the corresponding reference value. For example, when the value that reflects tumor-cytotoxic activity measured by the method described above is higher than the corresponding reference value, the tumor cells are determined to have been damaged. When the tumor-cytotoxic activity measured by the method described above is equal to or below the corresponding reference value, the tumor cells are determined to have not been damaged. The method for predicting the effect of a tumor immunotherapy is also a method for detecting a patient on whom the effect of a tumor immunotherapy is beneficial. The method for predicting the effect of a tumor immunotherapy is also a method for detecting a patient on whom the effect of a tumor immunotherapy is not beneficial.

The reference value can be any reference value as long as whether tumor cells are damaged can be determined on the basis of the reference value. For example, the reference value can be determined from the value of tumor-cytotoxic activity of negative control PBMCs in which tumor immunity is not activated and/or the value of tumor-cytotoxic activity of positive control PBMCs in which tumor immunity is activated. The method for measuring the value of tumor-cytotoxic activity of negative control PBMCs and the value of tumor-cytotoxic activity of positive control PBMCs is preferably the same as the method for measuring the value of tumor-cytotoxic activity of PBMCs of a patient who is a target of treatment. The reference value may be the upper limit of values of tumor-cytotoxic activity of negative control PBMCs; the lower limit of values of tumor-cytotoxic activity of positive control PBMCs; the median, average, or mode of the values of tumor-cytotoxic activity of negative control PBMCs and the values of tumor-cytotoxic activity of positive control PBMCs; etc. Alternatively, the reference value may be calculated using an ROC curve (receiver operating characteristic curve), discriminant analysis, mode method, Kittler method, 3-σ method, p-tile method, etc. In another embodiment, the reference value may be selected from a tumor-cytotoxic activity of 5%, 10%, 15%, 20%, 25%, 30%, 35%, or 40%.

When tumor cells are determined to have been damaged, a tumor immunotherapy is determined to be effective against the malignant tumor in the patient from whom PBMCs have been collected (the PBMCs for which tumor-cytotoxic activity has been measured). When tumor cells are determined to not be damaged, a tumor immunotherapy is determined to not be effective against the malignant tumor in the patient from whom PBMCs have been collected (the PBMCs for which tumor-cytotoxic activity has been measured).

In the present specification, unless otherwise mentioned, the explanation of terms in this section is incorporated in the explanation of other embodiments of the present specification, the claims, and figures in its entirety.

2. A Test Reagent and a Kit for Predicting the Effect of a Tumor Immunotherapy

The second embodiment of the present invention relates to a test reagent for predicting the effect of a tumor immunotherapy comprising at least an engager described in section 1 above. The test reagent may contain, for example, a buffer for dissolving the engager. The buffer may contain a reducing agent for stabilizing the engager (e.g., β-mercaptoethanol and dithiothreitol), a surfactant, albumin, etc. The buffer may also contain an antiseptic, such as sodium azide. The engager may be in a dry form or dissolved in the buffer.

The third embodiment of the present invention relates to a kit for predicting the effect of a tumor immunotherapy comprising the test reagent. The kit in this embodiment comprises at least the test reagent according to the third embodiment and information, such as a protocol in which a measurement method using the test reagent is described, or URL or Q code for accessing the protocol.

3. A Prediction Device for Predicting the Effect of a Tumor Immunotherapy

The fourth embodiment of the present invention relates to a prediction device for predicting the effect of a tumor immunotherapy. Specifically, the prediction device comprises at least a processing unit; the processing unit obtains a measurement value of tumor-cytotoxic activity from tumor cells that directly or indirectly contacted with peripheral blood mononuclear cells collected from a patient who is a target for treatment of a malignant tumor in vitro, determines whether the tumor cells are damaged on the basis of the measurement value, and determines that the tumor immunotherapy is effective against the malignant tumor in the patient when the tumor cells are determined to have been damaged.

Figure 3:
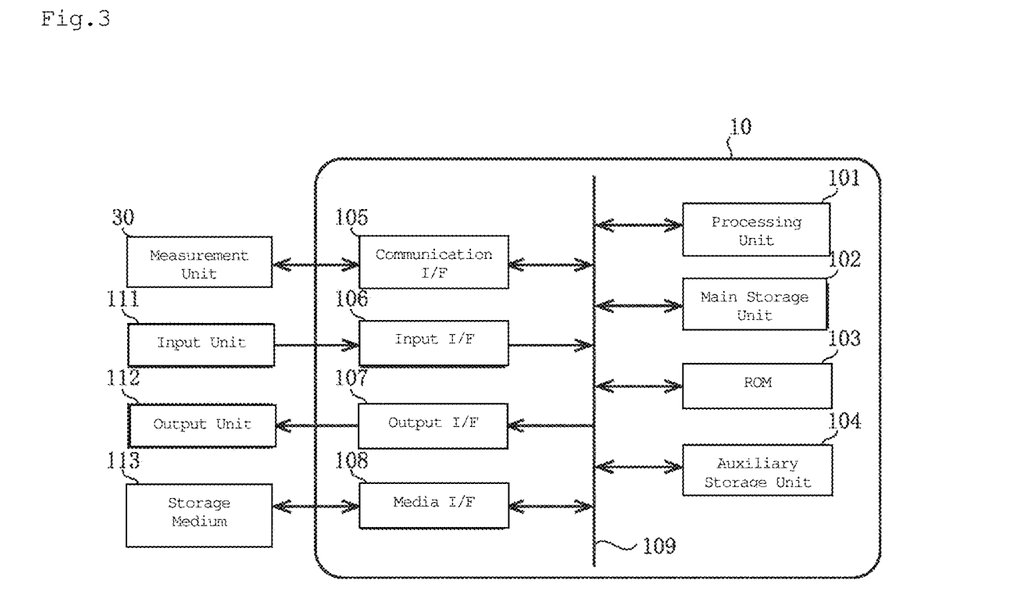
FIG. 3 is a block diagram illustrating the configuration of hardware of the prediction device.

FIG. 3 illustrate the configuration of hardware of a prediction device 10. The prediction device 10 may be connected to an input unit 111, an output unit 112, and a storage medium 113. The prediction device 10 may also be connected to a measurement unit 30 that includes a microplate reader etc. Specifically, the prediction device 10 may constitute a prediction system for predicting the effect of a tumor immunotherapy in which the prediction device 10 is connected directly or, for example, via a network to the measurement unit 30.

In the prediction device 10, a CPU 101, a main storage unit 102, a ROM (read-only memory) 103, an auxiliary storage unit 104, a communication interface (I/F) 105, an input interface (I/F) 106, an output interface (I/F) 107, and a media interface (I/F) 108 are connected to each other via a bus 109 so that data communication is possible. The main storage unit 102 and the auxiliary storage unit 104 together may be simply called "storage unit."

The CPU 101 is a processing unit of the prediction device 10. The prediction device 10 functions due to the CPU 101 that executes a computer program stored in the auxiliary storage unit 104 or the ROM 103 to process the obtained data.

The ROM 103 includes mask ROM, PROM, EPROM, EEPROM, or the like, and stores a computer program executed by the CPU 101 and data for use in this execution of the program. The CPU 101 may be an MPU 101. The ROM 103 stores a boot program that is executed by the CPU 101 when the prediction device 10 is booted and/or a program and settings for the operation of hardware of the prediction device 10.

The main storage unit 102 includes RAM (random-access memory), such as SRAM or DRAM. The main storage unit 102 is used in reading the computer programs saved in the ROM 103 and in the auxiliary storage unit 104. The main storage unit 102 is used as a workspace when the CPU 101 executes these computer programs.

The auxiliary storage unit 104 includes a semiconductor memory device, such as a hard disk and a flash memory, or an optical disk. The auxiliary storage unit 104 stores various computer programs to be executed by the CPU 101, such as an operating system and application programs, and various setting data used in executing the computer programs. Specifically, the auxiliary storage unit 104 stores a reference value etc. in a non-volatile manner.

The communication I/F 105 includes a serial interface, such as USB, IEEE 1394, and RS-232C, a parallel interface, such as SCSI, IDE, and IEEE 1284, an analog interface composed of a D/A converter or an A/D converter, or a network interface controller (NIC), etc. Under the control of the CPU 101, the communication I/F 105 receives data from the measurement unit 30 or other external device, and transmits or displays the information stored or generated by the prediction device 10 to the measurement unit 30 or outside as necessary. The communication I/F 105 may communicate with the measurement unit 30 or another external device via a network.

The input I/F 106 includes, for example, a serial interface such as USB, IEEE 1394, and RS-232C, a parallel interface such as SCSI, IDE, and IEEE 1284, or an analog interface composed of a D/A converter or an A/D converter. The input I/F 106 receives, for example, a character input, a click, or a voice input from the input unit 111. The received input content is stored in the main storage unit 102 or the auxiliary storage unit 104.

The input unit 111 includes, for example, a touchscreen, a keyboard, a mouse, a pen tablet, and/or a microphone, and performs character input or voice input on the prediction device 10. The input unit 111 may be externally connected to the prediction device 10 or may be integrated with the prediction device 10.

The output I/F 107 includes, for example, the same interface as that of the input I/F 106. The output I/F 107 outputs the information generated by the CPU 101 to the output unit 112. The output I/F 107 outputs the information that has been generated by the CPU 101 and that has been stored in the auxiliary storage unit 104 to the output unit 112.

The output unit 112 includes, for example, a display, a printer, or the like, and displays measurement results transmitted from the measurement unit 30, various operation windows in the prediction device 10, analysis results, and the like.

The media I/F 108 reads, for example, application software stored in the storage medium 113. The read application software, for example, is stored in the main storage unit 102 or the auxiliary storage unit 104. The media I/F 108 writes the information generated by the CPU 101 on the storage medium 113. The media I/F 108 writes the information that has been generated by the CPU 101 and that has been stored in the auxiliary storage unit 104 on the storage medium 113.

The storage medium 113 includes, for example, a flexible disk, CD-ROM, DVD-ROM, or the like. The storage medium 113 is connected to the media I/F 108 by a flexible disk drive, a CD-ROM drive, a DVD-ROM drive, or the like. The storage medium 113 may store an application program for the computer to execute an operation, and the like.

The CPU 101 may obtain application software and various settings necessary for control of the prediction device 10 via a network instead of reading them out from the ROM 103 or the auxiliary storage unit 104. The application program is stored in an auxiliary storage unit of the server computer on the network. The prediction device 10 can access the server computer, download the computer program, and store the computer program in the ROM 103 or the auxiliary storage unit 104.

The ROM 103 or the auxiliary storage unit 104 has installed in it an operation system that provides a graphical user interface environment, such as Windows® manufactured and sold by Microsoft Corporation in the United States. The application program according to the second embodiment is assumed to be operated on this operating system. Specifically, the prediction device 10 can be a personal computer or the like.

Figure 4:
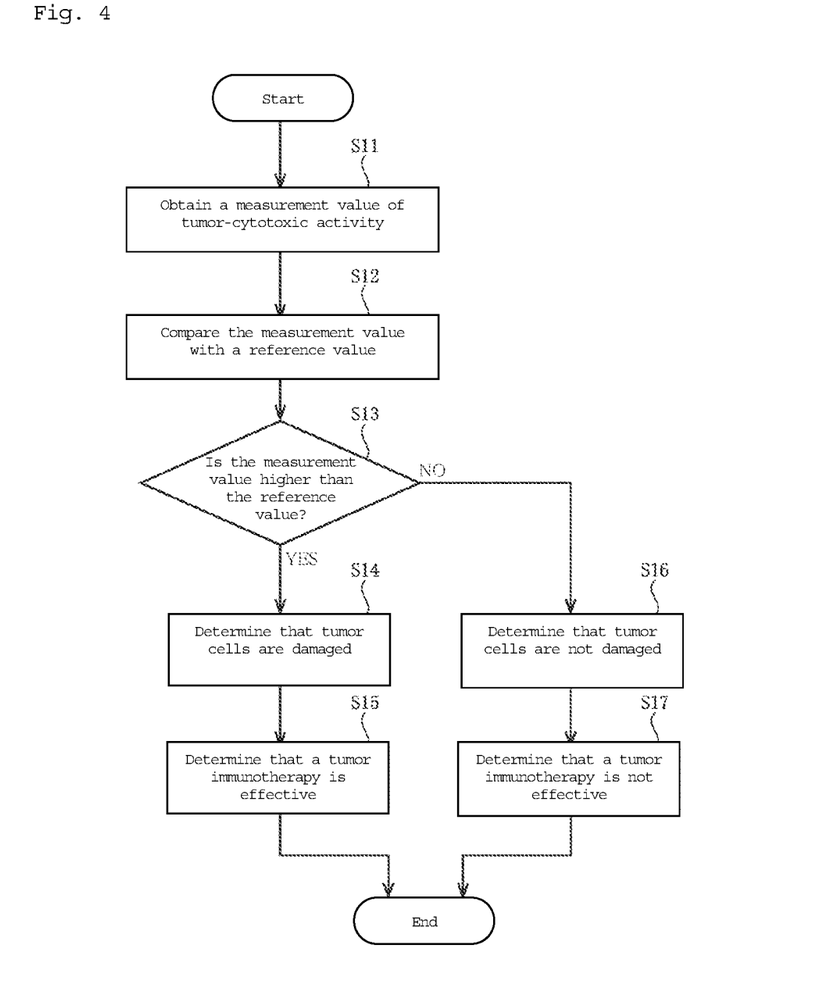
FIG. 4 is a flowchart of the process performed by the processing unit of the prediction device.

Below, the operation of the prediction device 10 is described with reference to FIG. 4. The operation of the prediction device 10 is controlled by the processing unit 101 of the prediction device 10 in accordance with a computer program for predicting the effect of a tumor immunotherapy described later.

First, the processing unit 101 obtains the measurement value of tumor-cytotoxic activity, which is obtained by the method described in section 1 above and which is input by a test operator from the input unit 111 (step S11). Alternatively, the processing unit 101 obtains information for calculating tumor-cytotoxic activity from the measurement unit 30. The information is such information that reflects the viable cell count of tumor cells that contacted with PBMCs (e.g., the absorbance of a living-cell-staining reagent).

Next, the processing unit 101 compares the measurement value obtained in step S11 with the reference value stored in the auxiliary storage unit 104 (step S12).

Subsequently, the processing unit 101 determines whether the tumor cells have been damaged on the basis of the comparison results in step S12 (step S13).

The processing unit 101 determines that the tumor cells are damaged in step S14 if the tumor cells have been damaged in step S13 (Yes), and further determines in step S15 that the tumor immunotherapy is effective against the malignant tumor in the patient from whom PMBCs have been collected. The processing unit 101 determines that the tumor cells are not damaged in step S16 if the tumor cells have not been damaged in step 13 (No), and further determines in step 17 that the tumor immunotherapy is not effective against the malignant tumor in the patient from whom PMBCs have been collected.

Although not shown in the figures, in step S13, the step of determining whether tumor cells are damaged may be divided into the step of obtaining a value that reflects the tumor-cytotoxic activity by measuring the tumor-cytotoxic activity of peripheral blood mononuclear cells that contacted with the tumor cells and the step of comparing the value that reflects the tumor-cytotoxic activity with the corresponding reference value and determining that the tumor cells are damaged when the measurement value is higher than the corresponding reference value.

For each embodiment of the step of determining whether tumor cells are damaged, the explanation of the step of determining whether tumor cells are damaged in section 1 above is incorporated here.

The processing unit 101 may output the results obtained in step S14 or step S16 from the output unit 112, or record the results in a recording medium 113.

4. A Computer Program for Predicting the Effect of a Tumor Immunotherapy and a Storage Medium that Stores the Computer Program The fifth embodiment of the present invention relates to a computer program for predicting the effect of a tumor immunotherapy. Specifically, the fifth embodiment of the present invention relates to a computer program for controlling the operation of the prediction device for predicting the effect of a tumor immunotherapy described in section 3 above.

The steps performed by the computer program of the fifth embodiment correspond to steps S11 to S16 described in section 3 above. The explanation of each step in section 3 above can be incorporated in the fifth embodiment.

Further, the sixth embodiment of the present invention relates to a storage medium that stores the computer program. Specifically, the computer program is stored in a storage medium, such as a semiconductor memory device, including a hard disk and a flash memory, or an optical disk. The storage format of the program in the storage medium can be any format as long as the devices described above can read the program. The storage in the storage medium is preferably non-volatile.

EXAMPLES

The present invention is described in detail with reference to the Examples below. However, the present invention is not limited to the Examples in interpretation of the invention.

I. Example 1: Measurement of Tumor-Cytotoxic Activity Using Peripheral Blood Mononuclear Cells 1. Method
(1) U251 cell line was suspended in a RPMI1640 medium containing 10% FBS (a 10% FBS-supplemented RPMI1640 medium) such that the cell count of U251 cell line was $1 \times 10^5$/mL, thereby preparing a cell suspension. The cell suspension was seeded in a 96-well plate at a rate of 100 µL/well, and incubated in a wet incubator at 37° C. for 24 hours in the presence of 5% $CO_2$ gas.
(2) Peripheral blood (heparin blood collection) was collected from lung cancer patients, and a cell population containing peripheral blood mononuclear cells ("PBMC") was collected in accordance with the attached protocol using Lymphoprep™ (Alere Technologies AS). The collection of PBMCs was performed immediately before step (3) described below.
(3) The PBMCs and EphA2-CD3 BiTE® were added to the 96-well plate subjected to incubation in step (1) such that the cell count of the PBMCs was $5 \times 10^4$ per well, and the final concentration of EphA2-CD3 BiTE® was 100 ng/mL per well. For a control, only the PBMCs were added to the 96-well plate that was subjected to incubation in step (1), thereby preparing wells to which EphA2-CD3 BiTE® was not added. The amount of the 10% FBS-supplemented RPMI medium per well after the PBMCs and EphA2-CD3

BiTE® were added was 200 µL in total. After the PBMCs and EphA2-CD3 BiTE® were added, incubation was performed for 48 hours.

(4) After incubation, each well was washed with a 10% FBS-supplemented RPMI medium four times. After washing the wells, the medium was removed from the wells. 100 µL of a 10% FBS-supplemented RPMI medium and 20 µL of CellTiter 96® AQueous One Solution Reagent (MTS reagent: Promega Corporation) were added to each of the wells. Thereafter, the 96-well microplate was subjected to incubation in a wet incubator at 37° C. for 20 minutes in the presence of 5% carbon dioxide.

(5) The absorbance at 490 nm of each well of the 96-well microplate after completion of incubation in step (4) was measured with a microplate reader. Subsequently, tumor-cytotoxic activity was calculated in accordance with the following equation.

Absorbance of a well containing U251 cell line and PBMCs=A
Absorbance of a well containing U251 cell line, PBMCs, and EphA2-CD3 BiTE=B $$\text{Tumor-cytotoxic activity (\%)}=[(A-B)/A]\times 100$$

2. Results

Figure 5:
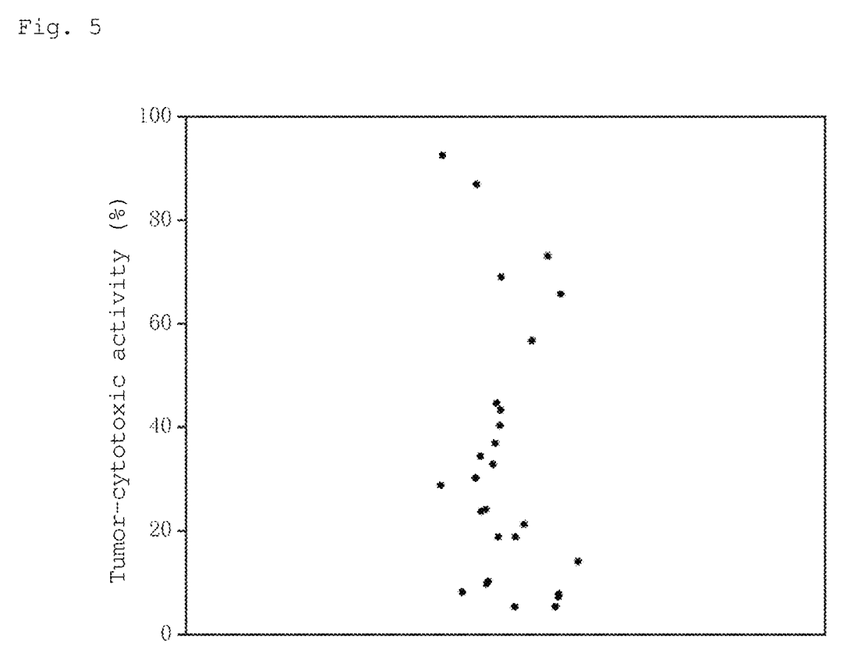
FIG. 5 illustrates the tumor-cytotoxic activity of PBMC in patients with lung cancer.

FIG. 5 illustrates the tumor-cytotoxic activity of PBMCs of each patient. Because BiTE for use was one that binds to CD3, the tumor-cytotoxic activity of the PBMCs was assumed to be the tumor-cytotoxic activity of peripheral blood T cells. As seen from FIG. 5, the tumor-cytotoxic activity of peripheral blood T cells of the lung cancer patients varies depending on the individual patients. While some patients exhibited a few percent of tumor-cytotoxic activity, some patients exhibited a tumor-cytotoxic activity as high as 80% or higher. This indicates that the tumor-cytotoxic activity of peripheral blood T cells of the patients varies from person to person.

II. Experimental Example 1: Tumor-Cytotoxic Activity of T Cells in Lung Cancer Tissue The tumor-cytotoxic activity of T cells in a lung cancer tissue was measured in accordance with the following method by collecting cells from a lung cancer tissue and measuring the cytotoxic activity of the cell population. A cancer tissue was transferred to a 6-cm dish and minced. The tissue was then placed in a tissue agitation solution (a Tumor Dissociation Kit (Miltenyi Biotec) was added to HBSS(-)+ 2% FBS+10 mM HEPES) and stirred with a gentleMACS™ Dissociator (Miltenyi Biotec), followed by incubation in an incubator maintained at 37° C. for 30 minutes with the incubator rotated. Thereafter, the stirred cell-containing solution was filtered through a 70-µm mesh to filter the tissue residue, and the filtrate was centrifuged at 600×g for 10 minutes to collect the precipitate. BD Pharm lyse (BD Biosciences) was added to the precipitate containing the cells, and the mixture was left for 2 minutes. A HBSS buffer was then added to the cell-containing solution after being left, and centrifugation was performed at 600×g for 10 minutes, thereby collecting a precipitate again. A 30% Percoll solution was added to the recollected precipitate, and the mixture was centrifuged at 12000×g for 30 seconds, thereby recollecting a precipitate. The recollected precipitate was washed with a HBSS buffer and centrifuged at 12000×g for 30 seconds, thereby collecting the cells in the tissue. The tumor-cytotoxic activity of the collected cells was measured by the same method as in section 1 above. Because BiTE for use was one that binds to CD3, the tumor-cytotoxic activity of the cells collected from this lung cancer tissue was assumed to be the tumor-cytotoxic activity of T cells in the lung cancer tissue.

III. Example 2: Repertoire Analysis of T-cell Receptor

To confirm whether T-cell clones common in the tumor and in peripheral blood were present in the same patient, a repertoire analysis of T-cell receptor (TCR) was performed. CD8+ T cells were isolated from peripheral blood PBMCs and cells in the lung cancer tissue of a lung cancer patient using the FACSAria (Becton Dickinson). RNA was extracted from the isolated CD8+ T cells, and TCR gene was amplified using Adaptor-Ligation PCR, followed by determining the base sequence using a next-generation sequencer. The TCR repertoire analysis was outsourced to Repertoire Genesis, Inc. (World wide web at repertoire.co.jp/detailed_repertoire.html). A repertoire analysis was performed on TCRα and TCRβ. The repertoires of the top 30 clones in occurrence frequency in PBMCs and T cells in lung cancer tissues were compared between patients 1 to 4.

Figure 6:
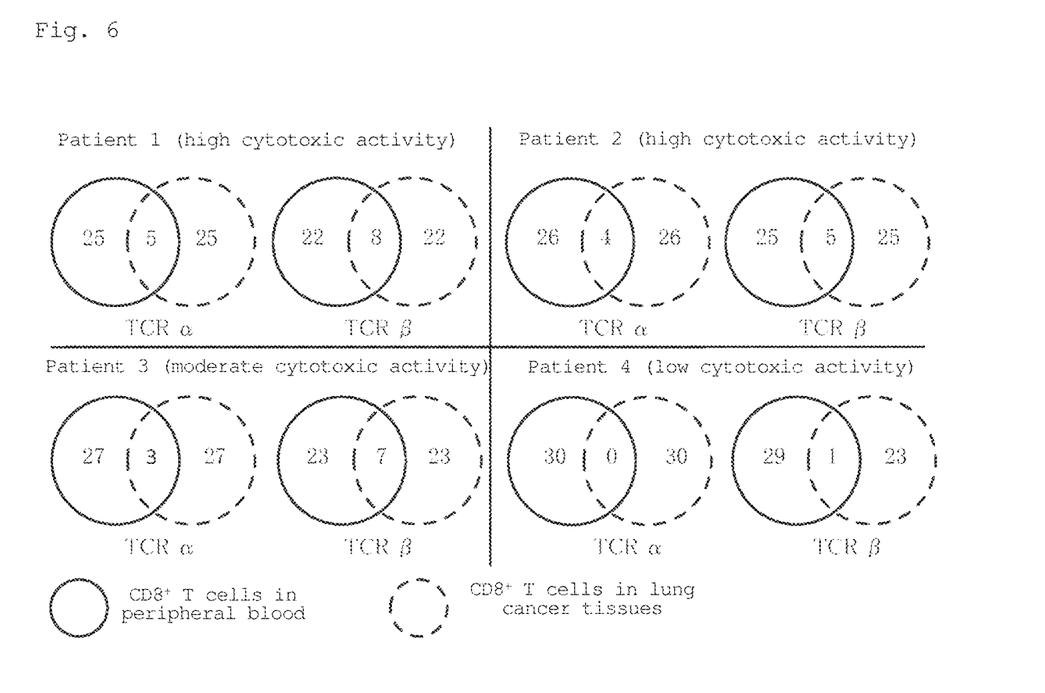
FIG. 6 shows the results of a repertoire analysis of CD8+ T cells in peripheral blood and CD8+ T cells in lung cancer tissues.

Patient 1 and patient 2 are examples of high tumor-cytotoxic activity of CD8+ T cells in lung cancer tissues. Patient 3 is an example of moderate tumor-cytotoxic activity. Patient 4 is an example of low tumor-cytotoxic activity. FIG. 6 illustrates the results.

A comparison of the repertoires of the top 30 clones in occurrence frequency revealed that patients 1 to 3, who exhibited a high or moderate tumor-cytotoxic activity of T cells in the lung cancer tissues, had multiple types of common clones of CD8+ T cells in their peripheral blood and lung cancer tissues. In contrast, patient 4, who exhibited a low tumor-cytotoxic activity of T cells in the lung cancer tissues, had only one common clone of CD8+ T cells in the peripheral blood and the lung cancer tissues. This suggests that the higher the tumor-cytotoxic activity of T cells in the lung cancer tissues, the more the cytotoxic T cells that have proliferated specifically to the tumor-cell-antigen in the lung cancer tissues appear in peripheral blood.

Figure 7A:
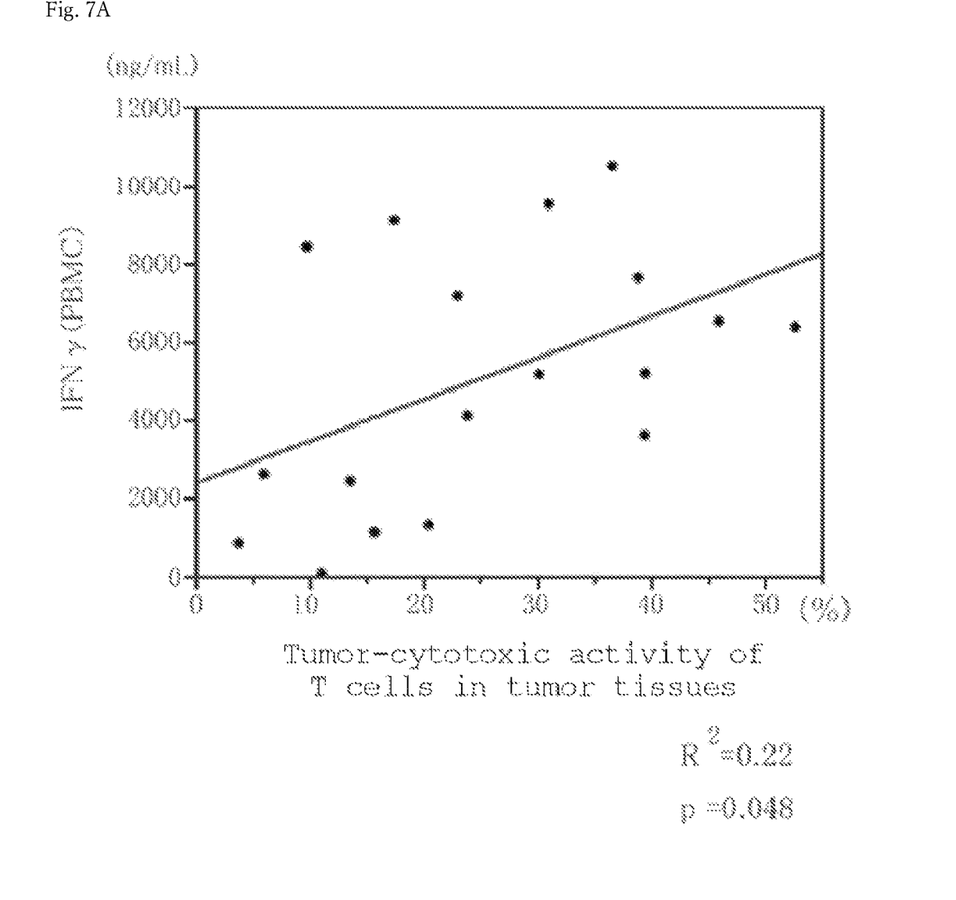
FIG. 7A depicts graphs illustrating a correlation between the tumor-cytotoxic activity of T cells in a tumor (lung cancer) tissue and the amount of IFNγ produced by PBMC via an engager.
Figure 7B:
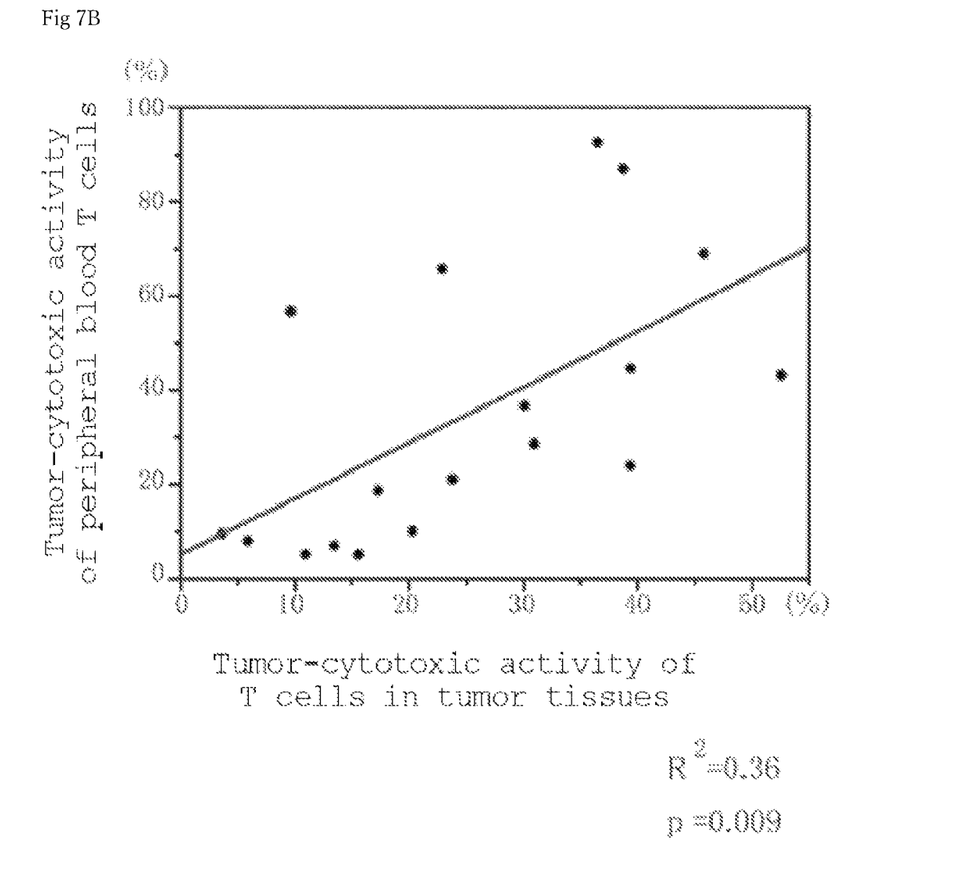
FIG. 7B depicts graphs illustrating a correlation between the tumor-cytotoxic activity of T cells in a tumor (lung cancer) tissue and the tumor-cytotoxic activity of T cells in peripheral blood.

IV. Example 3: A Correlation Between the Tumor-Cytotoxic Activity of T Cells in Lung Cancer Tissues and the Tumor-Cytotoxic Activity of Peripheral Blood T Cells Next, a correlation between the tumor-cytotoxic activity of T cells in lung cancer tissues and the tumor-cytotoxic activity of peripheral blood T cells derived from PBMCs was determined. FIG. 7 illustrates the results. The coefficient of correlation $R^2$ and the p value were determined using statistical software JMP. The p value indicates a test value as to whether a correlation is present.

For a comparison example, EphA2-CD3 BiTE was added to PBMCs collected from a patient and U251 cell line, and the mixture was cultured for 2 days to prepare a culture supernatant; the concentration of interferon γ (IFNγ) that exhibits anti-tumor activity was determined. The correlation between the results and the tumor-cytotoxic activity of T cells in lung cancer tissues was then determined. The concentration of IFNγ was measured using a Bio-Plex Pro human cytokine GI 27-plex panel (Bio-Rad).

The results indicate that the correlation between the tumor-cytotoxic activity of T cells in lung cancer tissues and the tumor-cytotoxic activity of peripheral blood T cells was $R^2=0.36$ with p=0.009, suggesting that the cytotoxic activity of peripheral blood T cells reflects the tumor-cytotoxic activity of T cells in lung cancer tissues. In IFNγ, $R^2$ was 0.22, with p=0.048, indicating that IFNγ also correlates the tumor-cytotoxic activity of T cells in lung cancer tissues. However, this reveals that the tumor-cytotoxic activity of peripheral blood T cells shows a stronger correlation with the tumor-cytotoxic activity of T cells in lung cancer tissues than IFNγ.

From these results, it was inferred that the tumor-cytotoxic activity of T cells in tumor tissues can be predicted by measuring the tumor-cytotoxic activity of peripheral blood T cells, and that the effect of a tumor immunotherapy thus can be predicted by measuring the tumor-cytotoxic activity of PBMCs in peripheral blood.

V. Example 4: A Correlation Between the Effect of Nivolumab and the Tumor-Cytotoxic Activity of Peripheral Blood T Cells 1. Method A comparison was made between the tumor-cytotoxic activity of peripheral blood T cells derived from PBMCs measured in accordance with Example 1 and the effect of nivolumab in 18 patients. The effect of nivolumab was evaluated by the method described below. In accordance with the method in Example 1, U251 cell line was seeded in a 96-well plate and incubated at 37° C. for 24 hours in a wet incubator in which 5% $CO_2$ gas was present. The cells in lung cancer tissues of each patient (cell count: $5 \times 10^4$/well) collected in accordance with the method described in Experimental Example 1 and 1 μg/ml of nivolumab (provided from Ono Pharmaceutical Co., Ltd), together with 100 ng/ml of EphA2-CD3 BiTE®, were added to each well. For a negative control, 1 μg/ml of human IgG4 (Abcam PLC), instead of nivolumab, was added to a medium, together with 100 ng/ml of EphA2-CD3 BiTE®. The absorbance was measured in accordance with the method described in Example 1 using a CellTiter 96® AQueous One Solution Reagent (MTS reagent: Promega Corporation), and tumor-cytotoxic activity was calculated using the following equation.

Absorbance in a well containing U251 cell line, cells in lung cancer tissues, negative control, and EphA2-CD3 BiTE=A Absorbance in a well containing U251 cell line, cells in lung cancer tissues, nivolumab, and EphA2-CD3 BiTE=B Tumor-cytotoxic activity (%)=[(A−B)/A]×100

The coefficient of correlation $R^2$ and the p value were determined using statistical software JMP. The p value indicates a test value as to whether a correlation is present.

2. Results

Figure 8A:
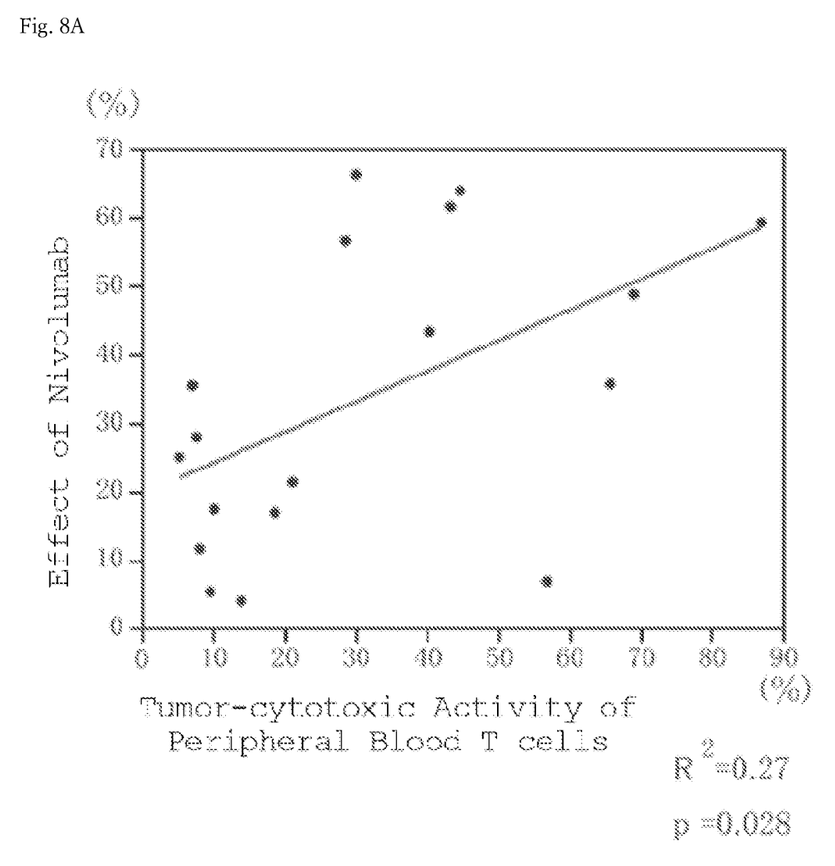
FIG. 8A depicts graphs illustrating a correlation between the effect of nivolumab in T cells in a tumor (lung cancer) tissue and the tumor-cytotoxic activity of T cells in peripheral blood when the cutoff value of tumor-cytotoxic activity of T cells in peripheral blood is 28%.
Figure 8B:
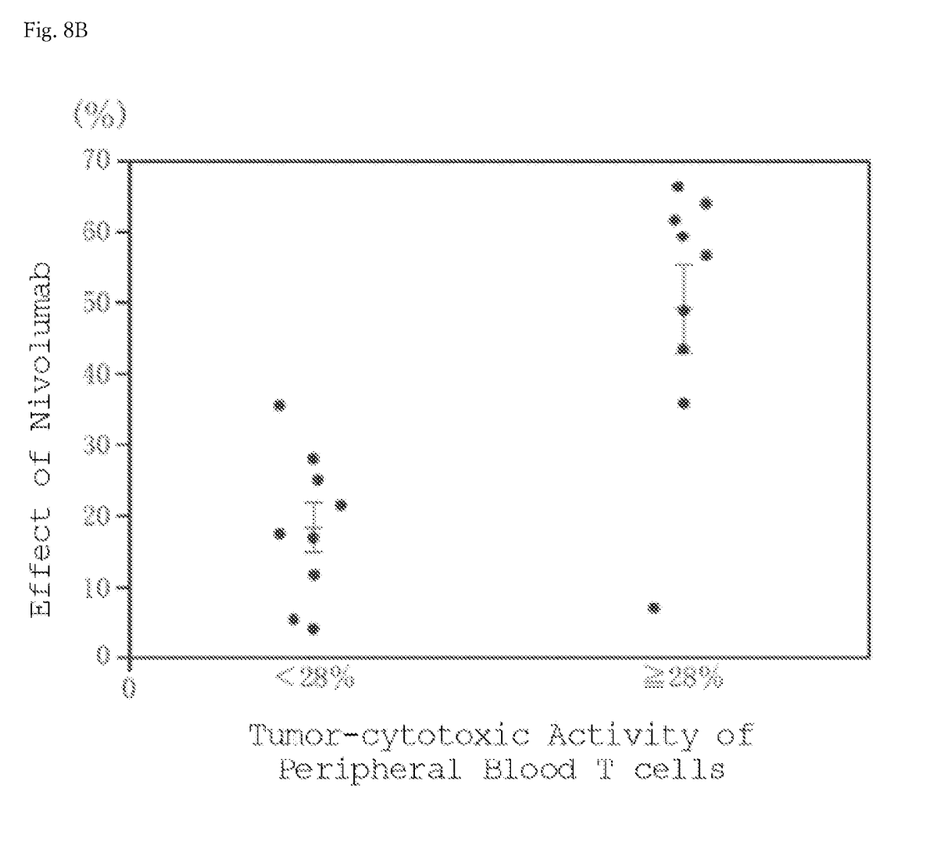
FIG. 8B shows the effect of nivolumab in T cells in a tumor (lung cancer) tissue of each group when the cutoff value of tumor-cytotoxic activity of T cells in peripheral blood is 28%.

FIG. 8A illustrates the correlation between the effect of nivolumab and the tumor-cytotoxic activity of peripheral blood T cells. $R^2$ was 0.27, with p=0.028, indicating that the effect of nivolumab correlates with the tumor-cytotoxic activity of PBMCs. The patients were divided into 2 groups: one group including 9 patients in order from one that exhibited the highest tumor-cytotoxic activity of peripheral blood T cells, and the other group including the remaining 9 patients. A tentative cutoff value determined from the ROC curve was 28%. A significant difference test for the effect of nivolumab was performed between these 2 groups; the p value was 0.0005, which indicated that the effect of nivolumab was significantly higher in the group with higher tumor-cytotoxic activity of peripheral blood T cells (FIG. 8B).

This reveals that the tumor-cytotoxic activity of peripheral blood T cells measured using PBMCs is highly correlated with the effect of a tumor immunotherapy. Additionally, this indicates that the tumor-cytotoxic activity of peripheral blood T cells is usable as an evaluation marker for the effect of a tumor immunotherapy.

VI. Example 5: A Correlation Between the Tumor-Cytotoxic Activity of Peripheral Blood T Cells and the Effect of a Tumor Immunotherapy Next, a correlation between the tumor-cytotoxic activity of peripheral blood T cells derived from PBMCs of lung cancer patients and the effect of a tumor immunotherapy was examined. The tumor-cytotoxic activity of PBMCs collected from patients was measured in accordance with Example 1, and then 3 patients with tumor-cytotoxic activity of 25% or higher were selected. A reduction in tumor size was observed in these 3 patients due to the tumor immunotherapy using an anti-PD-1 antibody, and the duration of therapy was more than 140 days; i.e., long-term therapy was possible. This reduction in tumor size and continued therapy indicate that the tumor immunotherapy was effective.

Currently, when determining whether a tumor immunotherapy should be applied, a positive rate of PD-L1-expressing cells in tumor tissues is used as an index. Thus, the positive rate of PD-L1-expressing lung-cancer cells in tumor tissues of the three patients was measured. Whereas two of the patients had a positive rate of 50% or higher, the one remaining patient exhibited a positive rate as significantly low as 2%. The positive rate of PD-L1-expressing cells was evaluated by performing immunostaining (immunological antibody technique) of PD-L1 protein. It is not predicted from immunostaining of PD-L1 protein whether a tumor immunotherapy is effective for the patient with only 2% PD-L1-expressing cells.

However, whether peripheral blood T cells of the patient with only 2% PD-L1-expressing cells damage tumor cells can be determined by measuring the tumor-cytotoxic activity of peripheral blood T cells derived from PBMCs of the patient. In fact, the effect of a tumor immunotherapy was observed in such a patient. Thus, the method for predicting the effect of a tumor immunotherapy according to this disclosure would enable the prediction of whether a tumor immunotherapy is applicable even to a patient with a low positive rate of PD-L1-expressing cells. Moreover, the method for predicting the effect of a tumor immunotherapy according to this disclosure would be able to detect a patient in whom a tumor immunotherapy is effective at a higher detection rate than immunostaining of PD-L1 protein.

DESCRIPTION OF THE REFERENCE NUMERALS

101 processing unit
10 prediction device

The invention claimed is:
1. A method for detecting a patient for whom tumor immunotherapy is effective and treating the patient detected, which method comprises:
    contacting peripheral blood mononuclear cells (PBMCs) from a patient having a malignant tumor with tumor cells under in vitro test conditions consisting of an engager and a culture medium to thereby obtain a test group, wherein the engager crosslinks a cytotoxic T cell with the tumor cells and the tumor cells are a cultured cell line of a malignant tumor, and the engager is a bispecific or trispecific antibody contacting the PBMCs with the tumor cells under in vitro negative control conditions consisting of the culture medium to thereby obtain a negative control group, obtaining a tumor-cytotoxic activity value of T cells, wherein the tumor-cytotoxic activity value is determined by comparing a viable cell count of the tumor cells after contact with the PBMCs under the in vitro test conditions to a control viable cell count of the tumor cells after contact with the PBMCs under the in vitro negative control conditions, wherein the tumor-cytotoxic activity value corresponds to the degree to which T cells of the PBMCs have damaged tumor cells under the in vitro test conditions, comparing the tumor-cytotoxic activity value of the T cells with a corresponding reference value, and determining that the tumor immunotherapy is effective for the patient when the value is higher than the corresponding reference value, and administering an effective amount of the tumor immunotherapy to the patient for whom the tumor immunotherapy is determined to be effective, wherein the engager is not the tumor immunotherapy for the patient, wherein a concentration of interferon γ (IFNγ) correlating with tumor-cytotoxic activity of T cells is not determined, and wherein the tumor immunotherapy increases the tumor-cytotoxic activity of T cells.

2. The method according to claim 1, wherein the bispecific antibody contains an antigen-binding domain that binds to one member of T-cell surface antigens and an antigen-binding domain that binds to one member of surface antigens of the tumor cells.

3. The method according to claim 1, wherein the tumor-cytotoxic activity value of the T cells is determined from the following equation:

Tumor-cytotoxic activity value (%)={([viable cell count of tumor cells in the negative control group]−[viable cell count of tumor cells in the test group])/[viable cell count of tumor cells in the negative control group]}×100.

4. The method according to claim 1, wherein the tumor immunotherapy is selected from the group consisting of an immune checkpoint antibody inhibitor therapy; an adoptive immunotherapy; a cytokine therapy; a tumor vaccine therapy; and a bispecific antibody therapy.

5. The method according to claim 4, wherein the immune checkpoint antibody inhibitor comprises at least one selected from the group consisting of an anti-PD1 antibody, an anti-PD-L1 antibody, an anti-CCR4 antibody, an anti-CTLA-4 antibody, an anti-Tim3 antibody, and an anti-LAG3 antibody.

6. The method according to claim 3, wherein the corresponding reference value of the tumor-cytotoxic activity value is at least 28%.

7. The method according to claim 5, wherein the immune checkpoint antibody inhibitor is nivolumab.

8. The method according to claim 1, wherein the malignant tumor of the patient is a respiratory-system malignant tumor.

* * * * *